United States Patent
Bray, Jr.

(10) Patent No.: US 8,317,841 B2
(45) Date of Patent: Nov. 27, 2012

(54) CERVICAL DYNAMIC STABILIZATION SYSTEM

(76) Inventor: Robert S. Bray, Jr., Studio City, CA (US)

( * ) Notice: Subject to any disclaimer, the term of this patent is extended or adjusted under 35 U.S.C. 154(b) by 722 days.

(21) Appl. No.: 11/859,210

(22) Filed: Sep. 21, 2007

(65) Prior Publication Data

US 2008/0077141 A1 Mar. 27, 2008

Related U.S. Application Data

(60) Provisional application No. 60/826,979, filed on Sep. 26, 2006.

(51) Int. Cl.
*A61B 17/80* (2006.01)
*A61B 17/70* (2006.01)
(52) U.S. Cl. .......... 606/283; 606/282; 606/286
(58) Field of Classification Search .............. 606/70–71, 606/279–299, 902–906
See application file for complete search history.

(56) References Cited

U.S. PATENT DOCUMENTS

| | | | | |
|---|---|---|---|---|
| 5,415,661 | A | * | 5/1995 | Holmes .................. 606/255 |
| 6,228,085 | B1 | * | 5/2001 | Theken et al. ............... 606/289 |
| 6,293,949 | B1 | | 9/2001 | Justis et al. |
| 6,342,055 | B1 | * | 1/2002 | Eisermann et al. ......... 623/17.16 |
| 2002/0013586 | A1 | * | 1/2002 | Justis et al. ..................... 606/61 |
| 2002/0123750 | A1 | * | 9/2002 | Eisermann et al. .............. 606/69 |
| 2004/0102773 | A1 | | 5/2004 | Morrison et al. |
| 2005/0043732 | A1 | | 2/2005 | Dalton |
| 2005/0124992 | A1 | * | 6/2005 | Ferree ............. 606/61 |
| 2005/0149020 | A1 | * | 7/2005 | Jahng ............... 606/61 |
| 2005/0171539 | A1 | * | 8/2005 | Braun et al. .................. 606/61 |
| 2005/0261774 | A1 | * | 11/2005 | Trieu ......................... 623/17.16 |
| 2006/0058792 | A1 | * | 3/2006 | Hynes ............................. 606/61 |

FOREIGN PATENT DOCUMENTS

WO 2005062902 A2 7/2005

* cited by examiner

*Primary Examiner* — Kevin T Truong
*Assistant Examiner* — Larry E Waggle, Jr.
(74) *Attorney, Agent, or Firm* — Cooper Legal Group LLP

(57) ABSTRACT

A vertebral stabilization plate assembly is provided. The plate assembly includes a flexible core located in a mid-portion section of the plate assembly; at least a first and a second attachment portion positioned above and below (or above and below—depending on orientation of flexible core) the flexible core, wherein the first and the second attachment portions comprise a plurality of fastener holes through which a plurality of fasteners are inserted to attach the plate assembly to at least two vertebral bone structures; and at least one flexible cable that extends through at least a first portion of the flexible core to maintain a position of the flexible core within the plate assembly, wherein the plate assembly is weight-bearing and attaches to the at least two vertebral bone structures and extends across a disc space located between the at least two vertebral bone structures.

26 Claims, 3 Drawing Sheets

CERVICAL DYNAMIC STABILIZATION SYSTEM

CROSS-REFERENCE TO RELATED APPLICATIONS

This application claims the benefit of U.S. Provisional Application Ser. No. 60/826,979, entitled CERVICAL DYNAMIC STABILIZATION SYSTEM and filed on Sep. 26, 2006, the entirety of which is incorporated herein by reference.

BACKGROUND OF THE INVENTION

1. Field of the Invention

The present invention relates in general to a vertebral stabilization implant. In particular, the present invention relates to a vertebral column dynamic stabilization device that supplements vertebral stabilization via the anterior column and/or the middle column lip and that can also facilitate disc regeneration.

2. Description of Related Art

Each vertebra has a cylindrical-shaped vertebral body in the anterior portion of the spine with an arch of bone to the posterior that covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

When a surgeon is faced with a ruptured disc but not necessarily a severely degenerative segment, traditionally a microdiscectomy is performed where a simple removal of the disc fragment is performed and the fragment is removed from the cord. One problem with this solution is although the endplates of the disc and the lateral portions of the disc may be left intact; there can be a collapse of the spine, with excessive collapse of the interspace in height. This can lead to secondary neural foraminal stenosis.

Other solutions involve flexible rod attachments. For example, a posterior system for the lumbar spine with a pedicle screw base system and a flexible rod attachment is known as the Zimmer Spine Dynesis System. The Zimmer system though is a posterior system and has no application in the cervical spine or for anterior applications.

Recent solutions have looked at the possibility of replacing the disc in an interdiscal position with a motion device, which involves total disc replacement, and there are multiple devices on the market and patented available for this use. Other solutions involve cervical plates that provide rigid stabilization of an anterior column. These concepts aid fusion with a supplementation of stability after a bone graft is placed into the disc space. The stabilization of the vertebra to allow fusion is often assisted by a surgically implanted device to hold the vertebral bodies in proper alignment and allow the bone to heal. However, there are disadvantages to these current stabilization devices.

SUMMARY OF THE INVENTION

In accordance with one aspect of the present invention, a device as described in further detail below provides a flexible plate that allows partial sharing of the weight of the vertebral bodies to promote bone healing or support at partial discectomy. A bone will not heal if it is stress-shielded from all weight bearing. If a partial discectomy is not supported, then it will collapse. Therefore, one aspect of the subject application provides a device that is strong enough to resist collapsing forces or abnormal angulation during the healing of the bone and/or disc.

In accordance with another aspect, the present invention provides a dynamic stabilization device which includes a weight bearing plate and a flexible core. According to yet another aspect of the present invention, an anterior column dynamic stabilization device is provided which allows supplementation of stabilization via the anterior column. The flexible core is located in the midportion of the plate and is mobile in all planes of motion, allowing six planes of motion to mimic a natural motion of the neck. The plate may include attachment features such as caps, screws, and a lip to provide additional stability.

According to another aspect of the present invention, anterior column stabilization and/or stabilization of the middle lip of the vertebral body column is provided. Due to the placement and structure of a stabilization plate, disc regeneration is also facilitated. In one embodiment, the plate or device stabilizes the vertebrae, such as in a patient's neck, in an "open" position, preventing a subsequent collapse after partial removal of disc material. With the vertebrae stabilized in the open or height-maintained position, the disc material is allowed to fibrose in naturally over a healing period (e.g., six-to-eight-week period) to yield regeneration and fibrosis of the disc in the open space between the vertebrae. Due to the structure of the stabilization plate, the motion segment is preserved. After the disc has fibrosed in or regenerated, the plate can also provide some additional stability to the segment in the absence of fusion.

It is to be appreciated that the present invention is distinctly different from an artificial disc, which involves replacement of a disc with a mechanical device when a total discectomy is performed. Rather, the subject invention can supplement the patient's natural disc and adds stability to the anterior and/or middle column lip to facilitate disc regeneration. Furthermore, the subject invention may be used to supplement fusion of a disc with partial weight sharing of the bone. The subject invention is also different from any type of nuclear replacement, which is a biologic or gel replacement of the disc nucleus. That is, the present invention can allow the disc to heal naturally as opposed to requiring a nuclear replacement.

According to still another aspect of the invention, a vertebral stabilization plate assembly that facilitates anterior columnar stabilization is provided. The plate assembly comprises a flexible core located in a mid-portion section of the plate assembly; at least a first and a second attachment portion positioned above and below the flexible core, wherein the first and the second attachment portions comprise a plurality of fastener holes through which a plurality of fasteners are inserted to attach the plate assembly to at least two vertebral bone structures; and at least one flexible cable that extends through at least a first portion of the flexible core to maintain a position of the flexible core within the plate assembly, wherein the plate assembly is weight-bearing and when attached to the at least two vertebral bone structures, extends across a disc space located between the at least two vertebral bone structures.

According to another aspect of the invention, a vertebral stabilization plate assembly that facilitates anterior columnar stabilization is provided. The plate assembly includes a flexible core located in a mid-portion section of the plate assembly; at least a first and a second attachment portions positioned above and below and at least partially overlapping the flexible core, wherein the first and the second attachment portions comprise a plurality of screw holes through which a plurality of screws are inserted to attach the plate assembly to at least two vertebral bone structures; and a plurality of caps having a general U-shaped configuration that each fit around top and bottom end portions of the flexible core, wherein the plate assembly is weight-bearing and when attached to the at least two vertebral bone structures, the plate assembly has a compression capability that holds a disc space located between the at least two vertebral bone structures open while still allowing compression, rotation, flexion, and extension that mimics natural movement of the at least two vertebral bone structures, thereby preventing collapse of the disc space.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF THE INVENTION

A plate of the present invention can be used to facilitate disc regeneration and vertebral stabilization as well as to provide supplementation to a bone graft. The subject plate can also supplement stabilization for fusion and/or can allow partial weight bearing or weight loading in a dynamic way to a bone graft. Furthermore, the plate can provide partial protection from extrusion or over-collapse, thus allowing the bone to regenerate or heal at a faster rate via Wolff's law. Conventional cervical plates employ mechanical weight bearing and require the use of a titanium plate but lack a plate having a flexible core that permits the full range of motion in six planes.

As mentioned above, the present invention can have non-fusion applications, such as when a standard discectomy is performed in a conventional manner, but where anterior column secondary stability is desired to prevent any over-collapse of the space. Additionally, the present invention can be applied to tissue regeneration technology to allow stabilization of a disc space in an open, non-collapsed position, thereby allowing regeneration of the disc.

More specifically, the present invention can involve a stabilization plate that includes a flexible core portion which permits not only a full range of motion but also permits the plate to bear weight. Having a plate assembly helps to promote natural healing of a disc after partial surgical excision of a disc or injury to a disc. Unlike conventional spinal implants or devices, no other implant is needed to assist in the weight-bearing forces such as during the healing period.

For example, the stabilization plate as described herein has a compression capability to hold a surgical space open at approximately 6-7 mm in height while still allowing compression, rotation, flexion, and extension in approximately the 5-7 degree range and allowing approximately 2-3 mm of motion in any plane. The stiffness of the stabilization plate can be determined by the density selection of the flexible core material of the plate.

It is possible that the present invention may allow for potential applications in stem cell technology, cartilage regenerative injection technology, or subsequent stabilization for biomaterials for nuclear implants. Each of these devices and/or injections requires stabilization of an injured segment in a neutral position and can apply the flexible core of the present invention. It is to be appreciated that in these other applications, the flexible core will not necessarily create fusion or regeneration, unless bone or bone generation materials are also provided. The subject application will now be described in further detail with reference to FIGS. 1-7.

Figure 1:
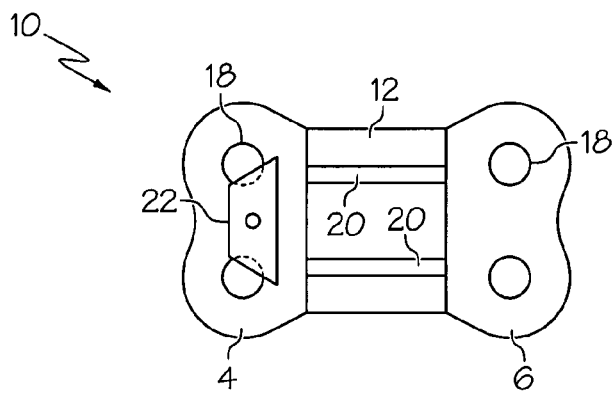
FIG. 1 is a front or top view of a first embodiment of the present invention.

Referring now to FIG. 1, a plate assembly 10 includes a flexible core 12 with attachment portions 4, 6 above and below (or adjacent to either side of) the flexible core 12. In an embodiment, the attachment portions 4, 6 are comprised of a metal. The attachment portions 4, 6 can be made of titanium or other suitable metals. Alternatively, the attachment portions 4, 6 may be comprised of a hard material that is non-metallic. A plurality of screws can be placed in the vertebral body in a plurality of screw-holes 18 (or other fastener-holes 18) that correspond to each attachment portion 4, 6 located above and below the flexible core 12. It should be appreciated that the attachment portions 4, 6 can also be described as being positioned at each opposite end of the flexible core and/or in end portions of the plate assembly. The attachment portions 4, 6 have a width that can be larger than the flexible core 12. The attachment portions 4, 6 contain the screw-holes 18 to allow attachment of a plurality of screws to the plate assembly 10 and to a bone structure without the occurrence of any pull-through. A cover lock 22 can be provided to ensure that the screws do not back-out of the screw-holes 18.

In addition, a plurality of cover locks can be added in any embodiment described herein and also are used to prevent the displacement of the flexible core 12. In an example embodiment, the flexible core 12 comprises a dense but mobile plastic. It is to be appreciated that other flexible and/or elastic materials may be used. For example, the flexible core may include a soft gel material. Also, the flexible core 12 may be multi-component and/or multi-material. In general, the flexible core 12 with the flexible/elastic properties allows the six planes of motion to mimic a natural motion of the vertebrae. The flexible core 12 may be maintained in position with at least one flexible cable 20, which extends through the flexible core 12. In the shown example, there are two flexible cables. However, a different number of cables (e.g., none, one or more than two) may be used. The flexible cables 20 can be made of titanium or other strong but flexible materials. The flexible cables 20 assist in providing resistance to forces that rotate, flex, and extend the flexible core 12. The flexible core 12 may also be made of a biologically compatible material and may act as a flexible central bumper.

Figure 2:
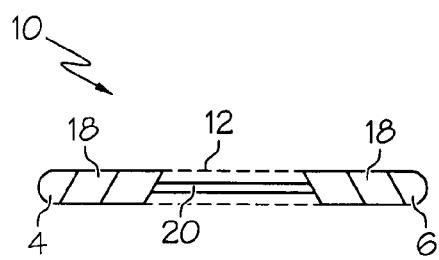
FIG. 2 is a side view of the first embodiment of the present invention.

Turning now to FIG. 2, a side view of the first embodiment is shown. One flexible cable 20 can be seen in relatively the middle portion of the flexible core 12. In other embodiments, the flexible cable 20 may be in locations other than the middle portion of the flexible core 12. In this embodiment, the flexible core 12 extends between each attachment portion 4, 6 and extends across multiple vertebrae.

Figure 3:
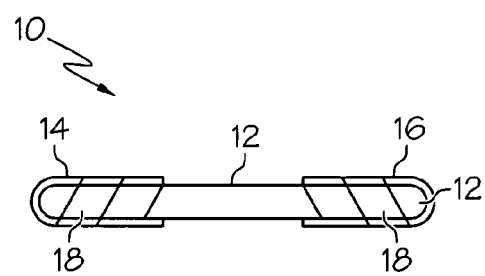
FIG. 3 is a side view of a second embodiment of the present invention.

A side view of another embodiment is illustrated in FIG. 3. In this embodiment, caps 14, 16 fit around the two end portions (or top and bottom portions depending on the orientation of the flexible core 12) of the flexible core 12 and have a generally U-shaped configuration. The caps 14, 16 in this embodiment can have a width that is larger than the width of the flexible core 12. The flexible core 12 extends across multiple vertebrae. Furthermore, the flexible core 12 can extend almost the entire length of the plate assembly 10 due to the shape and orientation of the caps 14, 16.

Figure 4:
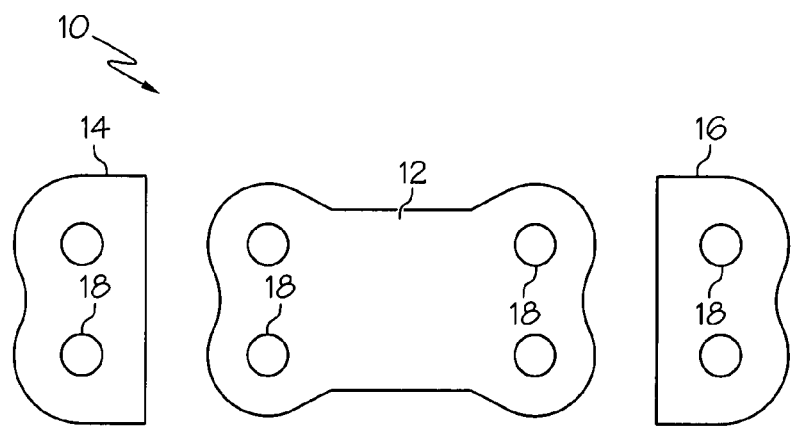
FIG. 4 is an expanded front or top view of the second embodiment of the present invention.

FIG. 4 shows an embodiment that demonstrates one way to assemble the plate assembly 10. In this embodiment, the caps 14, 16 are shown oriented in the manner in which they will be assembled onto the flexible core 12. The screw-holes 18 on each cap 14, 16 correspond to screw-holes 18 located on the flexible core. An initial step in assembling this embodiment is to ensure that each cap (14, 16) is oriented onto the flexible core 12 to permit the entry of screws. This orientation will only be performed once the plate assembly 10 is in the proper location for purposes of supplementation of a bone graft. Once screws are inserted into each screw-hole 18, the plate assembly 10 is thus assembled.

Figure 5:
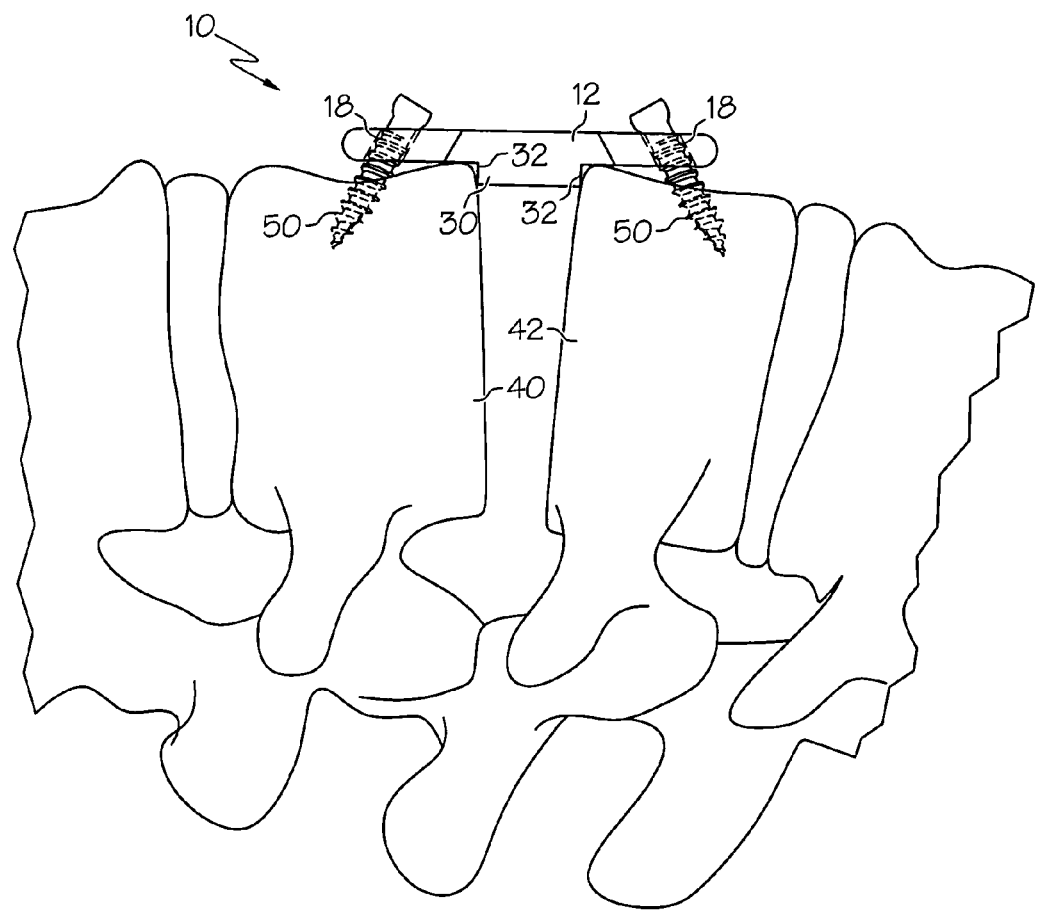
FIG. 5 is an expanded side view of an embodiment of the present invention that contains a lip portion on the flexible core of the plate assembly as it may appear in relation to two vertebrae.

In yet another embodiment, according to FIG. 5, the flexible core 12 contains a lip 30 as illustrated when implanted into two vertebral bone structures 40, 42. The lip 30 extends from the flexible core 12 into an area located between two rigid vertebral bone structures 40, 42. The lip 30 contains edges 32 that mate with the corresponding edges 32 of the vertebral bone structures 40, 42. The lip 30 can extend slightly from the anterior column into the middle column of a vertebral body, under the lips of the vertebral body. However, the lip 30 does not extend well into the disc space or replace any disc in any way. The lip 30 extends slightly to engage the anterior column lips for further stability of the flexible core 12. This embodiment also shows that screws 50 can be used to connect the plate assembly 10 to the vertebral bone structures 40, 42. It is to be appreciated that in other embodiments, other fastener devices may be used in place of the screws 50.

Figure 6:
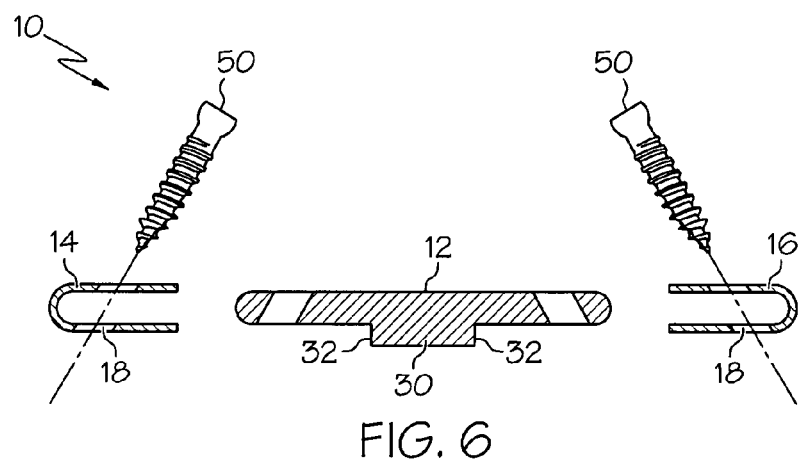
FIG. 6 is an expanded side view of another embodiment of the present invention that contains a lip portion on the flexible core of the plate assembly and FIG. 7 is a front or top view of an embodiment of the present invention as it may appear in relation to two vertebrae.

Referring now to FIG. 6, an assembly is shown that contains a flexible core 12 with a lip 30. The lip contains edges 32 that mate with the corresponding edges of vertebrae structures. The edges 32 can be comprised of an angular edge as in FIG. 6 or an edge that is formed from a substantially right angle, as in FIG. 5. The embodiment in FIG. 6 also contains caps 14, 16 that fit around the two end portions of the flexible core 12; and the caps 14, 16 have a generally U-shaped configuration. The flexible core 12 extends across multiple vertebrae (e.g., at least two vertebrae). In addition, the flexible core 12 extends almost the entire length of the plate assembly 10 due to the shape and orientation of the caps 14, 16. Though screws 50 can be used to connect the plate assembly 10 to the vertebrae structure as shown, it should be understood that other fastener devices may be used in place of the screws 50.

Figure 7:
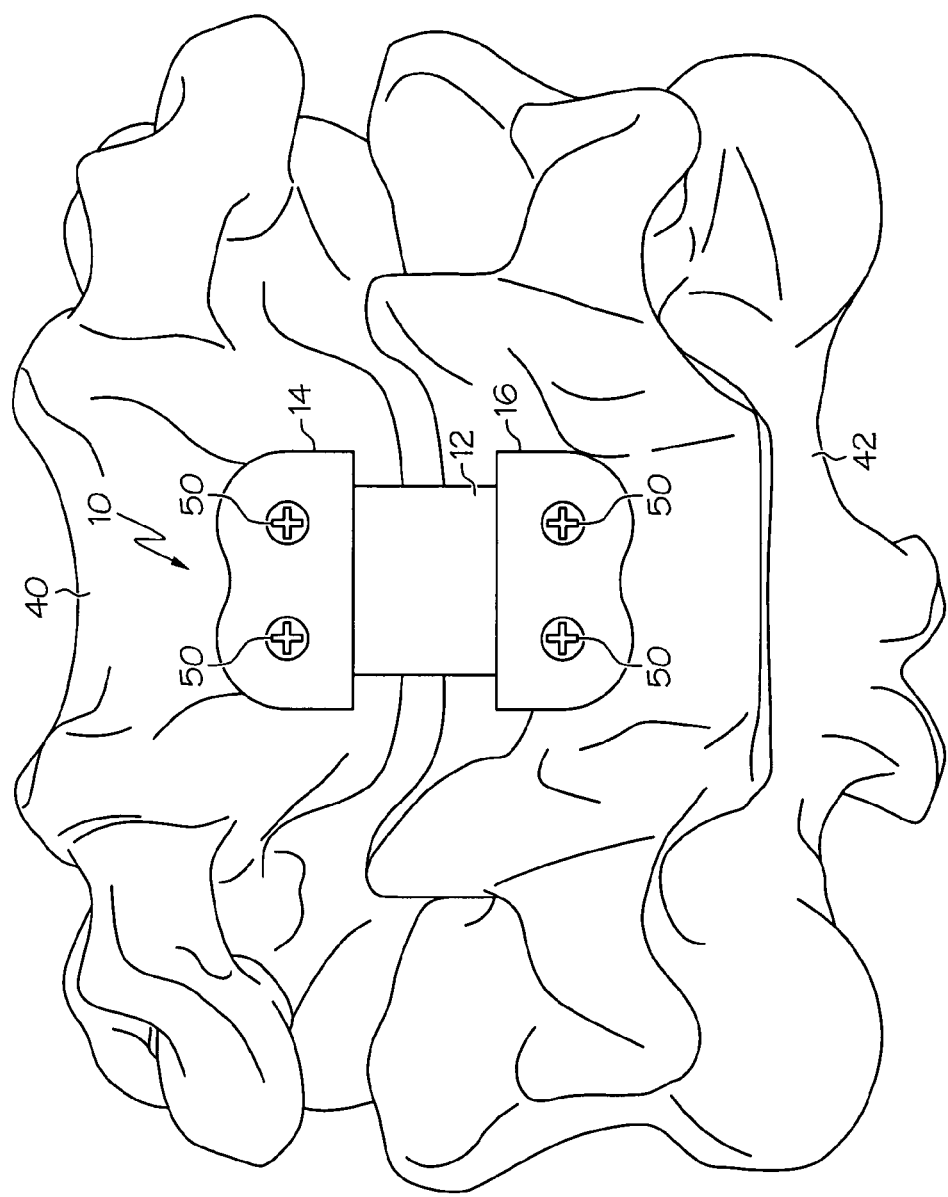

Furthermore, it should be appreciated that in any of the embodiments described herein, the shape of the flexible core 12 is generally rectangular to fit across multiple vertebrae. Other shapes for the flexible core 12 may be provided so long as the present invention fits across multiple vertebrae. FIG. 7 depicts a top view of an example stabilization plate assembly 10 attached to at least two vertebral bone structures 40, 42 via screws 50.

The present invention may be used in a cervical region or in application to the lower levels in the lumbar spine. For example, the present invention can be used in the L4-5 or L5-S1 vertebrae levels for supplementation of a disc injury, however, the profile, or height, of the flexible core and the plate should be kept to a minimum amount. Moreover, the plate assembly can be employed with respect to other parts of the spine as well. As mentioned above, cover locks can be added to any embodiment of the design to prevent the backout of any screw or fastener device and to prevent the displacement of the flexible core.

It should be evident that this disclosure is by way of example and that various changes may be made by adding, modifying or eliminating details without departing from the fair scope of the teaching contained in this disclosure.

What is claimed is:

1. A vertebral stabilization plate assembly that facilitates vertebral anterior columnar stabilization of a vertebral column, the plate assembly comprising:
    a flexible core located in a mid-portion section of the plate assembly, the flexible core extending in a first direction which is along an elongation direction of the vertebral column and extending in a second direction, transverse to the first direction and along a lateral direction with respect to the vertebral column;
    a first attachment portion and a second attachment portion positioned above and below the flexible core, respectively, wherein the first attachment portion includes a plurality of laterally-spaced fastener holes through which a plurality of fasteners are inserted to attach the first attachment portion to a first bone structure of the vertebral column and the second attachment portion includes a plurality of laterally-spaced fastener holes through which a plurality of fasteners are inserted to attach the second attachment portion to a second bone structure of the vertebral column; and
    a plurality of laterally-spaced flexible cables that extend from the first attachment portion to the second attachment portion within at least a first portion of the flexible core to maintain a position of the flexible core within the plate assembly, wherein the plate assembly is weight-bearing and when attached to the first and second vertebral bone structures, the plate assembly extends across a disc space located between the at least two vertebral bone structures.

2. The plate assembly of claim 1, wherein the flexible core comprises a dense and mobile material through which the flexible cable extends and that permits a range of motion in six planes to mimic a natural motion of the vertebral bone structures.

3. The plate assembly of claim 2, wherein the vertebral bone structures correspond to a neck portion on a mammalian or human body.

4. The plate assembly of claim 1, wherein the first and the second attachment portions each have a lateral width that is larger than the first portion of the flexible core within which the plurality of laterally-spaced flexible cables extend as measured in the same lateral direction.

5. The plate assembly of claim 1, wherein each of the plurality of flexible cables comprises a strong and flexible material that provides resistance to at least one of rotation, flexion, and extension forces exerted upon the flexible core.

6. The plate assembly of claim 1, wherein each of the plurality of flexible cables comprises titanium.

7. The plate assembly of claim 1, wherein the flexible core is non-metal elastic material and the plurality of flexible cables are metal and encased within the non-metal elastic material of the flexible core.

8. The plate assembly of claim 1, wherein the first and second attachment portions and the flexible core each extending to provide the plate assembly as generally flat for placement of the plate assembly against an anterior side of the vertebral column.

9. The plate assembly of claim 1, wherein the disc space is maintained in an open position, thereby allowing at least a portion of disc material to fibrose in the disc space, which is in a height-maintained position.

10. The plate assembly of claim 1, wherein the plate assembly has a compression capability to hold a surgical space open at approximately 6 mm to 7 mm in height while still allowing compression, rotation, flexion, and extension in a range of approximately 5 degrees to 7 degrees, thereby preventing collapse of the space.

11. The plate assembly of claim 1, wherein the flexible core provides a range of motion of approximately 2 mm to 3 mm in any one plane.

12. The plate assembly of claim 1, wherein the flexible core comprises a flexible biologically compatible material, and the first and second attachment portions include material not present in the flexible core.

13. The plate assembly of claim 1 further comprising a plurality of caps having a general U-shaped configuration that each fit around top and bottom end portions of the flexible core.

14. The plate assembly of claim 13, wherein the plurality of caps each have a width greater than the width of the flexible core.

15. The plate assembly of claim 13, wherein the plurality of caps are each oriented around the top and the bottom end portions of the flexible core to permit entry of the plurality of screws through the plurality of screw holes.

16. The plate assembly of claim 1, wherein the flexible core comprises a lip portion, wherein the lip portion extends from the flexible core into an area located between the at least two vertebral bone structures.

17. The plate assembly of claim 16, wherein the lip comprises edges that mate with corresponding edges of the vertebrae structures.

18. The plate assembly of claim 17, wherein the edges of the lip each are angled with respect to the flexible core.

19. The plate assembly of claim 17, wherein the edges each are formed at right angles with respect to the flexible core.

20. The plate assembly of claim 16, wherein the lip extends slightly from an anterior column into a middle column of a vertebral body to engage an anterior column lip of the vertebral body to further stabilize the flexible core.

21. The plate assembly of claim 1, further comprising a plurality of cover locks overlapping each of the plurality of fasteners to prevent back-out of the plurality of fasteners from the plurality of fastener holes.

22. The plate assembly of claim 1, wherein the flexible core does not include a mesh material.

23. The plate assembly of claim 1, wherein the flexible core does not include a spiral cut material, braid material or a combination thereof.

24. The plate assembly of claim 1, wherein the flexible core does not include metal.

25. The plate assembly of claim 1, wherein the flexible core is made of plastic.

26. The plate assembly of claim 1, wherein the flexible core is made of soft gel material.

* * * * *